(12) United States Patent
Wallroth et al.

(10) Patent No.: US 6,725,860 B2
(45) Date of Patent: Apr. 27, 2004

(54) MONITORING PROCESS FOR METERING DIFFERENT GASEOUS ANESTHETICS

(75) Inventors: Carl F. Wallroth, Lübeck (DE); Frank Gottschalk, Bargteheide (DE); Ernst-Günter Scharmer, Krummesse (DE); Helmut Thiemann, Perkasie, PA (US)

(73) Assignee: Dräger Medizintechnik GmbH, Lübeck (DE)

( * ) Notice: Subject to any disclaimer, the term of this patent is extended or adjusted under 35 U.S.C. 154(b) by 210 days.

(21) Appl. No.: 09/778,616

(22) Filed: Feb. 7, 2001

(65) Prior Publication Data

US 2002/0104534 A1 Aug. 8, 2002

(51) Int. Cl.⁷ .................. A61M 16/00; F16K 11/00; G05D 11/02
(52) U.S. Cl. .............. 128/203.25; 128/203.12; 128/203.24; 128/203.27; 128/200.24
(58) Field of Search ............. 128/200.24, 203.12, 128/203.13, 203.24, 203.23, 203.27

(56) References Cited

U.S. PATENT DOCUMENTS

| | | | | | |
|---|---|---|---|---|---|
| 4,345,612 A | * | 8/1982 | Koni et al. | ............ | 137/101.19 |
| 4,905,685 A | * | 3/1990 | Olsson et al. | .......... | 128/203.12 |
| 5,046,018 A | * | 9/1991 | Flewelling et al. | ......... | 364/497 |
| 5,231,591 A | * | 7/1993 | Flewelling et al. | ......... | 364/497 |
| 5,237,990 A | * | 8/1993 | Psaros et al. | .......... | 128/204.21 |
| 5,272,907 A | * | 12/1993 | Hakala | ........ | 73/23.2 |
| 5,649,531 A | * | 7/1997 | Heinonen | .............. | 128/203.12 |
| 5,699,788 A | * | 12/1997 | Lekholm et al. | ....... | 128/203.12 |
| 5,920,263 A | * | 7/1999 | Huttenhoff et al. | ......... | 340/573 |
| 5,967,141 A | * | 10/1999 | Heinonen | .............. | 128/203.12 |
| 6,076,392 A | * | 6/2000 | Drzewiecki | .................. | 73/23.2 |
| 6,142,147 A | * | 11/2000 | Head et al. | ............. | 128/204.21 |
| 6,250,132 B1 | * | 6/2001 | Drzewiecki | ................. | 73/23.2 |
| 6,272,905 B1 | * | 8/2001 | Drzewiecki | ................. | 73/53.01 |
| 6,289,891 B1 | * | 9/2001 | Cewers | .................. | 128/203.12 |
| 6,305,212 B1 | * | 10/2001 | Drzewiecki | ................. | 73/23.2 |
| 6,415,792 B1 | * | 7/2002 | Schoolman | ............ | 128/204.23 |

OTHER PUBLICATIONS

Merriam Webster's Collegiate Dictionary 10th ed. p. 26.*

* cited by examiner

Primary Examiner—Joseph Weiss
(74) Attorney, Agent, or Firm—McGlew and Tuttle, P.C.

(57) ABSTRACT

A monitoring process for the reliable metering of different gaseous anesthetics uses a gaseous anesthetic monitor designed as only a single-channel monitor for determining the concentration of only one gaseous anesthetic. The process also uses an associated gaseous anesthetic metering means.

20 Claims, 2 Drawing Sheets

MONITORING PROCESS FOR METERING DIFFERENT GASEOUS ANESTHETICS

FIELD OF THE INVENTION

The present invention pertains to a monitoring process for metering different gaseous anesthetics with a gaseous anesthetic monitor for determining the concentration of only one gaseous anesthetic with an associated gaseous anesthetic metering means Specifically, the present invention pertains to a monitoring process for metering different gaseous anesthetics with a single-channel gaseous anesthetic monitor, which is designed for determining the concentration of only one gaseous anesthetic. The concentration of the gaseous anesthetic being measured is determined here according to a suitable measurement process, especially according to an infrared optical measurement process for measuring the concentration-dependent absorption of the radiation emitted by a radiation source after passing through the gaseous anesthetic by way of a preset measuring path, e.g., in a measuring gas cuvette filled with the gas to be measured, especially in such a way that the measurement is resolved for the individual breaths, i.e., breath by breath.

BACKGROUND OF THE INVENTION

It has been known that multichannel gaseous anesthetic monitors can be used which make possible the determination of the concentrations of several different gaseous anesthetics in the mixture based on the absorption wavelengths specific of the individual gaseous anesthetics.

However, it is desirable, especially for cost reasons, to also use single-channel gaseous anesthetic monitors, but it must be ensured in this case that the patient being treated is supplied specifically and with the particular desired gaseous anesthetic in a correctly metered manner.

SUMMARY AND OBJECTS OF THE INVENTION

The object of the present invention is to provide a monitoring process for the metering of different gaseous anesthetics, where the subsequent use of different gaseous anesthetics is possible only after a specific intervention by the monitoring person.

According to the invention, a monitoring process is provided for metering different gaseous anesthetics with a gaseous anesthetic monitor for determining the concentration of only one gaseous anesthetic with an associated gaseous anesthetic metering means. The gaseous anesthetic monitor is switched on or is activated from a standby mode by a switching signal. The subsequent display for selecting a gaseous anesthetic is alternatively confirmed with either the selection of a new, second gaseous anesthetic, or of the first gaseous anesthetic used previously. A concentration measurement is performed with the measuring constants stored for the first gaseous anesthetic in the case of the selection of the first gaseous anesthetic. In the case of the selection of a second gaseous anesthetic, an alarm is triggered and the fact that a gaseous anesthetic mixture was selected is displayed, so that, either the alarm is acknowledged and the concentration measurement takes place with the measuring constants stored for the second gaseous anesthetic, or alternatively a corrected, third gaseous anesthetic is selected and the concentration measurement is subsequently performed with the measuring constants stored for the third gaseous anesthetic.

The gaseous anesthetics may be selected from the group comprising the gases halothane, enflurane, isoflurane, desflurane, and servoflurane. The gaseous anesthetics may be selected on the gaseous anesthetic monitor by means of a rotatable acknowledge switch or by means of contact-sensitive display screen segments. The gaseous anesthetic metering means may have one or more vapors with filling devices specific of the gaseous anesthetic. The concentration of the gaseous anesthetics may be measured according to an infrared optical or piezoelectric measurement process.

According to another aspect of the invention, a monitoring device is provided as single-channel gaseous anesthetic monitor designed as a single-channel monitor for the concentration measurement of only one gaseous anesthetic. The device meters different gaseous anesthetics with a gaseous anesthetic monitor for determining the concentration of only one gaseous anesthetic with an associated gaseous anesthetic metering means. The concentration of the gaseous anesthetic being measured is determined with a measurement device, especially with an infrared optical measurement device for measuring the concentration-dependent absorption of the radiation emitted by a radiation source after passing through the gaseous anesthetic by way of a preset measuring path, e.g., in a measuring gas cuvette filled with the gas to be measured, especially in such a way that the measurement is resolved for the individual breaths, i.e., breath by breath.

One essential advantage of the process is that with a gaseous anesthetic monitor in which only a single-channel monitor with respect to gaseous anesthetics can also be used, a mixing of different gaseous anesthetics, which is not intended by the monitoring person, is ruled out.

An exemplary embodiment of the present invention will be explained below on the basis of the only figure, which schematically shows the course of the process according to the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
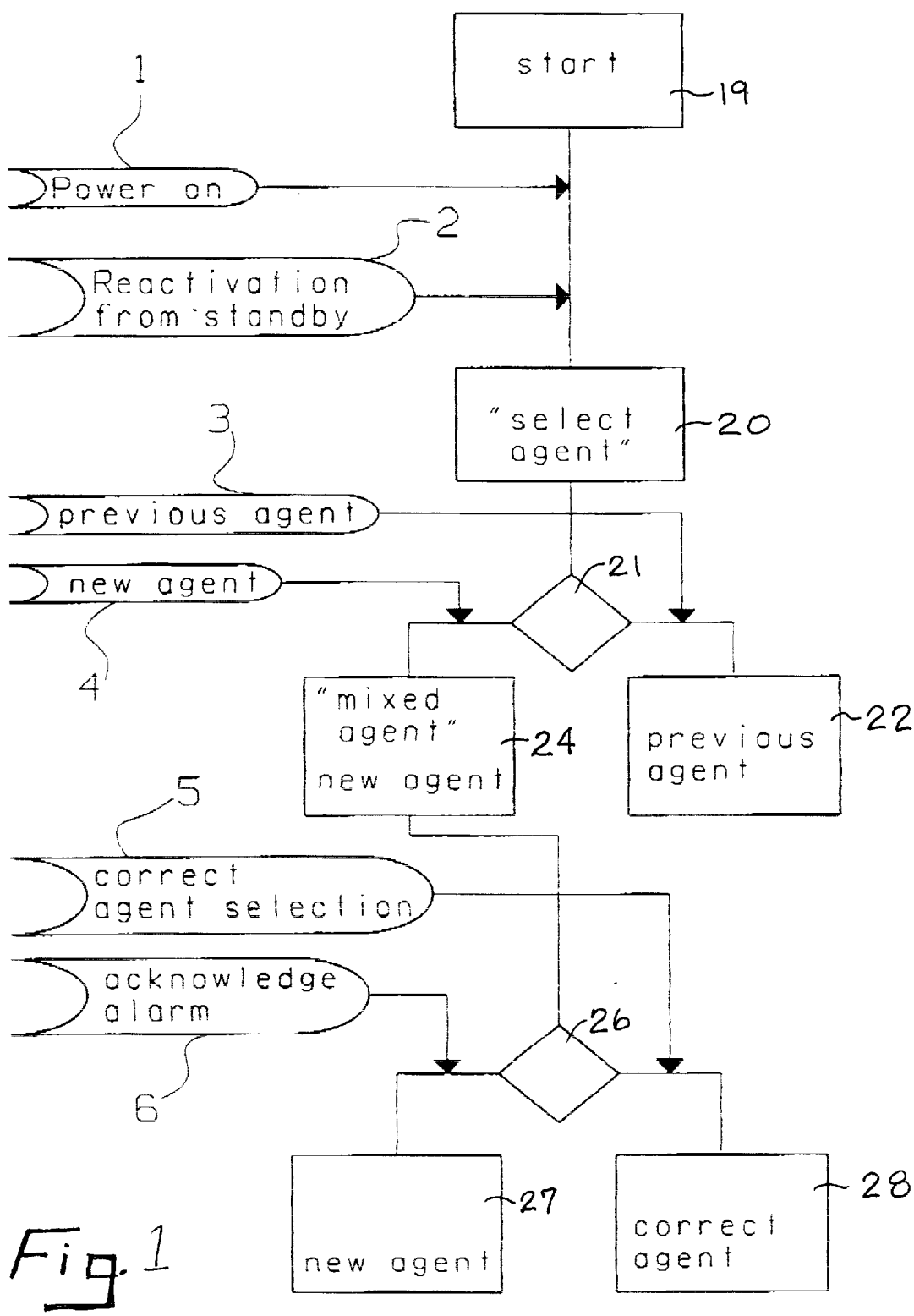
FIG. 1 is a process flow diagram of the process according to the invention.
Figure 2:
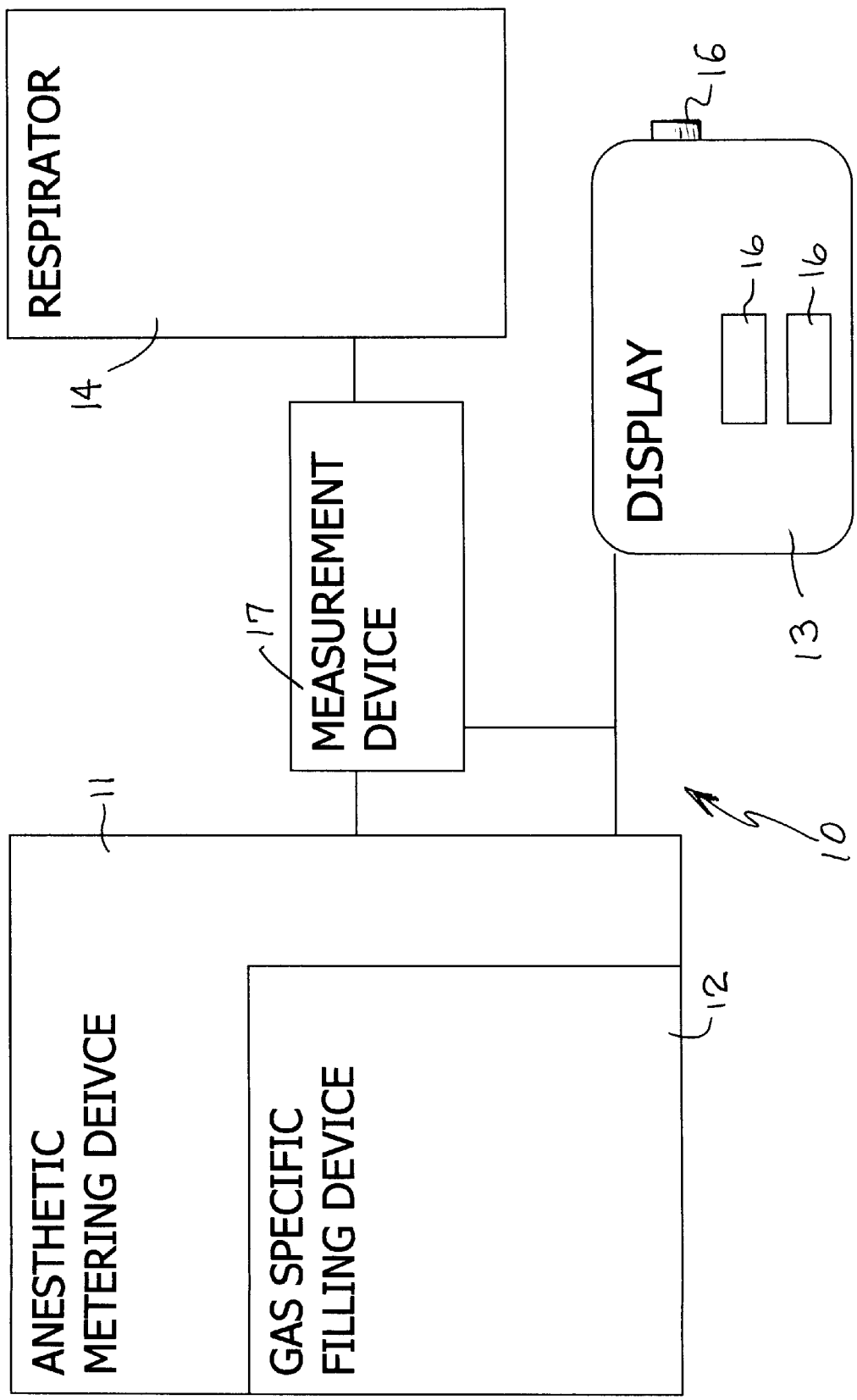
FIG. 2 is a diagram of the device according to the invention.

Referring to the drawings in particular, the reference numbers 1 through 6 denote interventions by the human operator based on the displays on the gaseous anesthetic monitoring device 10, which are shown schematically. The gaseous anesthetic monitoring device 10 is part of an anesthesia apparatus which has a respiration device 14, on the one hand, and gaseous anesthetic metering device 11 for the controlled release of one or different gaseous anesthetics, on the other hand. Gaseous anesthetic metering means contain, in general, gaseous anesthetic vapors, which are provided with gaseous anesthetic-specific filling devices 12 in order to ensure the filling of a specific vapor with one and the same, defined gaseous anesthetic only. A monitoring device 10 is provided for the single-channel 15 gaseous anesthetic monitor system designed as a single-channel monitor for the concentration measurement of only one gaseous anesthetic. A display 13 is a part of the monitoring device 10. The gaseous anesthetics may be selected on the gaseous anesthetic monitor by means of a rotatable acknowledge switch or by means of contact-sensitive display screen segments 16. The gaseous anesthetic metering device 11 may have one or more vapors with filling devices 12 specific of the gaseous anesthetic. The device 11 meters different gaseous anesthetics with a gaseous anesthetic monitor for determining the concentration of only one gaseous anesthetic with an associated gaseous anesthetic metering means. The concentration of the gaseous anesthetic being measured is determined with a measurement device 17, especially with an infrared optical measurement device 17 for measuring the concentration-dependent absorption of the radiation emitted by a radiation source after passing through the gaseous anesthetic by way of a preset measuring path, e.g., in a measuring gas cuvette filled with the gas to be measured, especially in such a way that the measurement is resolved for the individual breaths, i.e., breath by breath. The concentration of the gaseous anesthetics may be measured according to an infrared optical or piezoelectric measurement process.

Depending on the situation and the medical treatment, the respirated and anesthetized patient is supplied, e.g., before the surgery, with a gaseous anesthetic that is different from the one used directly during the surgery, so that a gaseous anesthetic mixture "mixed agent" is present in this case in the anesthesia apparatus during a certain transition period. This is usually known to the medically trained operating personnel.

The course of the process is as follows:

After switching on 1 the gaseous anesthetic monitor or after its reactivation 2 by the human operator from a standby mode indicated by "START" 19, there is a request to select a gaseous anesthetic "select agent" 20. Depending on the concrete situation, the human operator will select at 21 either the previous, first gaseous anesthetic 3 "previous agent" 22 or a new, second gaseous anesthetic 4 "new agent" 24, whereupon in the second case an optical and/or acoustic alarm 26 is triggered on the monitor. If the human operator selects the previous, first gaseous anesthetic 3, the gaseous anesthetic measurement is performed with the gas-specific constants stored for it. Since the gaseous anesthetic was not changed in the latter case, it is assumed in the algorithm on which the process is based that the formation of a mixture from two different gaseous anesthetics is not possible. If the human operator selected as an alternative another, second gaseous anesthetic 4 and the alarm is thereupon triggered, the human operator either must acknowledge the alarm 6 in the knowledge that a change of the gaseous anesthetic was intended "new agent" 27, associated with the appearance of a gaseous anesthetic mixture in the anesthesia apparatus during a certain transition period, or it is possible to correct the selection of the gaseous anesthetic 5 and to select a third gaseous anesthetic "correct agent" 28.

In both said cases of the selection of a second or a third gaseous anesthetic, there is a display "new agent," 28 "correct agent" 30 and the algorithm stored for the process activates the concentration measurement of the particular second or third gaseous anesthetic selected with the measuring constants stored for the particular gaseous anesthetic.

While a specific embodiment of the invention has been shown and described in detail to illustrate the application of the principles of the invention, it will be understood that the invention may be embodied otherwise without departing from such principles.

What is claimed is:

1. A monitoring device, comprising:

an anesthetic metering device;

a gas specific filling device connected to said anesthetic metering device;

a single-channel for supplying gas to a respirator;

a measurement device for determining the anesthetic concentration in said single channel wherein the measurement device has only a single-channel for the concentration measurement of only one gaseous anesthetic;

a display device connected to said measurement device, said display device querying an operator to select a gas for continued operation of said gas monitor, receiving an answer from the operator indicating a selected gas, comparing said selected gas to a previous gas, indicating an alarm if said selected gas is different than said previous gas, querying the operator to acknowledge a change in gas monitored by said gas monitor or to select another gas, receiving either an acknowledgment answer from the operator indicating acknowledgment of said change in gas, or a corrected answer selecting another gas;

said measurement device monitoring gas passing through said gas monitor according to measuring constants for said selected gas after said display device receives either said acknowledgment answer or said corrected answer.

2. A monitoring process for metering different gaseous anesthetics with a gaseous anesthetic monitor for determining the concentration of only one gaseous anesthetic with an associated gaseous anesthetic metering device, the process comprising the steps of:

switching the gaseous anesthetic monitor on or activating the monitor from a standby mode by a switching signal;

providing a subsequent display for selecting a gaseous anesthetic and one of selecting and confirming the selection of either a new, second gaseous anesthetic, or selection of the first gaseous anesthetic used previously;

performing a concentration measurement with the measuring constants stored for the first gaseous anesthetic, in the case of the selection of the first gaseous anesthetic;

triggering an alarm in the case of the selection of said new second gaseous anesthetic and displaying the fact that a gaseous anesthetic mixture was selected is displayed and one of: acknowledging the alarm wherein the concentration measurement takes place with the measuring constants stored for the new second gaseous anesthetic; or correcting the selection and selecting a third gaseous anesthetic and subsequently performing the concentration measurement with the measuring constants stored for said third gaseous anesthetic.

3. A monitoring process in accordance with claim 2, wherein the gaseous anesthetics are selected from the group comprising the gases halothane, enflurane, isoflurane, desflurane, and servoflurane.

4. A monitoring process in accordance with claim 3, wherein the gaseous anesthetics are selected on the gaseous anesthetic monitor by means of a rotatable acknowledge switch or by means of contact-sensitive display screen segments.

5. A monitoring process in accordance with claim 4, wherein the concentration of the gaseous anesthetics is measured according to an infrared optical or piezoelectric measurement process.

6. A monitoring process in accordance with claim 3, wherein the gaseous anesthetic metering device has one or more filling devices specific of gaseous anesthetics.

7. A monitoring process in accordance with claim 2, wherein the gaseous anesthetics are selected on the gaseous anesthetic monitor by means of a rotatable acknowledge switch or by means of contact-sensitive display screen segments.

8. A monitoring process in accordance with claim 7, wherein the gaseous anesthetic metering device has one or more filling devices specific of gaseous anesthetics.

9. A monitoring process in accordance with claim 3, wherein the concentration of the gaseous anesthetics is measured according to an infrared optical or piezoelectric measurement process.

10. A monitoring process in accordance with claim 2, wherein the gaseous anesthetic metering device has one or more filling devices specific of gaseous anesthetics.

11. A monitoring process in accordance with claim 10, wherein the concentration of the gaseous anesthetics is measured according to an infrared optical or piezoelectric measurement process.

12. A monitoring process in accordance with claim 2, wherein the concentration of the gaseous anesthetics is measured according to an infrared optical or piezoelectric measurement process.

13. A monitoring process in accordance with claim 4, wherein the gaseous anesthetic metering device has one or more filling devices specific of gaseous anesthetics.

14. A method in accordance with claim 2, wherein:

said acknowledging is performed by a human operator intervening with said gaseous anesthetic monitor.

15. A monitoring process for metering different gaseous anesthetics with a gaseous anesthetic monitor for determining the concentration of only one gaseous anesthetic with an associated gaseous anesthetic metering device, the process comprising the steps of:

using the aesthetic monitor with a first gas;

receiving an activation signal from an operator for the aesthetic monitor;

querying the operator to select a gas for continued operation of the monitor;

receiving an answer from the operator indicating a selected gas;

comparing said selected gas to said first gas;

triggering an alarm if said selected gas is different than said first gas and displaying that a gaseous anesthetic mixture was selected;

querying the operator to acknowledge a change in gas monitored by said gas monitor or to select another gas;

receiving an acknowledgment answer from the operator indicating acknowledgment of said change in gas;

measuring the concentration of gas passing through said gas monitor according to measuring constants for said selected gas.

16. A method in accordance with claim 15, wherein:

said measuring, receiving and querying are performed by said gas monitor.

17. A method in accordance with claim 15, wherein:

said gas monitor is a single channel gas monitor, a corrected answer is alternately receivable instead of said acknowledgment answer, said corrected answer indicating another gas for continued operation of the gas monitor;

said measuring of gas passing through the gas monitor being performed after receiving said corrected answer according to measuring constants for said another gas.

18. A method in accordance with claim 15, further comprising:

directly monitoring gas passing through said gas monitor according to measuring constants for said first gas, if said selected gas is identical to said first gas.

19. A process in accordance with claim 15, wherein:

said querying to acknowledge is performed after said triggering of said alarm;

said measuring according to said selected gas is performed after said receiving of said acknowledgment answer;

said querying to select a gas is performed after said receiving of said activation signal.

20. A method in accordance with claim 19, wherein:

all of said measuring, receiving and querying are performed by said gas monitor.

* * * * *